United States Patent
McWhorter et al.

(10) Patent No.: US 9,045,340 B2
(45) Date of Patent: Jun. 2, 2015

(54) STORAGE-STABLE AQUEOUS SOLUTIONS OF CHLORINE DIOXIDE AND METHODS FOR PREPARING AND USING THEM

(75) Inventors: Thomas Ellsworth McWhorter, Allentown, PA (US); Peter Kazlas, Allentown, PA (US); Madhu Anand, Allentown, PA (US); John Peter Hobbs, Lansdale, PA (US); Aaron A. Rosenblatt, New York, NY (US); Robert H. Shay, Allentown, PA (US); Barzin Keramati, Bethlehem, PA (US)

(73) Assignee: CDG ENVIRONMENTAL, LLC, Bethlehem, PA (US)

( * ) Notice: Subject to any disclaimer, the term of this patent is extended or adjusted under 35 U.S.C. 154(b) by 0 days.

(21) Appl. No.: 13/365,902

(22) Filed: Feb. 3, 2012

(65) Prior Publication Data

US 2012/0135167 A1    May 31, 2012

Related U.S. Application Data

(62) Division of application No. 12/296,049, filed as application No. PCT/US2006/060879 on Nov. 14, 2006.

(60) Provisional application No. 60/736,636, filed on Nov. 14, 2005.

(51) Int. Cl.
  *A61L 2/18* (2006.01)
  *C01B 11/02* (2006.01)

(52) U.S. Cl.
  CPC ......... *C01B 11/024* (2013.01); *Y10T 428/1352* (2015.01); *Y10T 428/1334* (2015.01); *Y10T 428/131* (2015.01); *Y10T 428/13* (2015.01); *C01B 11/028* (2013.01)

(58) Field of Classification Search
  CPC ............................ C01B 11/024; C01B 11/028
  USPC ............................................................. 422/37
  See application file for complete search history.

(56) References Cited

U.S. PATENT DOCUMENTS

| 2,309,457 | A | | 1/1943 | Hutchinson et al. |
| 4,430,226 | A | * | 2/1984 | Hegde et al. .................. 210/638 |
| 4,681,739 | A | | 7/1987 | Rosenblatt et al. |
| 4,853,270 | A | | 8/1989 | Wycech |
| 4,948,641 | A | | 8/1990 | Shantz et al. |

(Continued)

FOREIGN PATENT DOCUMENTS

WO    WO99/24356    5/1999

OTHER PUBLICATIONS

EPA Guidance Manual on Alernative Disinfectants and Oxidants: Chlorine Dioxide, Apr. 1999, pp. 4-1:4-41.*

(Continued)

*Primary Examiner* — Timothy Cleveland
(74) *Attorney, Agent, or Firm* — Ratnerprestia

(57) ABSTRACT

The present invention is for extremely pure solutions of chlorine dioxide, methods for making such solutions and to compositions and methods for storing, shipping and using such solutions. Generally, the chlorine dioxide solutions of the invention are aqueous solutions containing about 2500 ppm or less of total impurities. The chlorine dioxide solution can be prepare by passing dilute highly pure chlorine gas through a bed of substantially solid sodium chlorite and contacting the resulting chlorine dioxide gas with a liquid.

17 Claims, 9 Drawing Sheets

(56) References Cited

U.S. PATENT DOCUMENTS

| | | | |
|---|---|---|---|
| 5,006,326 A | | 4/1991 | Mayurnik |
| 5,039,423 A | | 8/1991 | Kelley |
| 5,110,580 A | | 5/1992 | Rosenblatt |
| 5,182,122 A | * | 1/1993 | Uehara et al. ............... 425/526 |
| 5,234,678 A | | 8/1993 | Rosenblatt et al. |
| 5,770,135 A | * | 6/1998 | Hobbs et al. ................. 264/83 |
| 5,855,861 A | * | 1/1999 | Lee ............................ 423/477 |
| 6,051,135 A | | 4/2000 | Lee et al. |
| 6,284,152 B1 | | 9/2001 | Kross |
| 2002/0037248 A1 | | 3/2002 | Bechberger et al. |
| 2003/0215381 A1 | | 11/2003 | Rosenblatt et al. |
| 2004/0022667 A1 | | 2/2004 | Lee |
| 2004/0211746 A1 | * | 10/2004 | Trude ........................... 206/508 |
| 2005/0079230 A1 | * | 4/2005 | Lee et al. ..................... 424/661 |
| 2007/0098591 A1 | | 5/2007 | Frinke |
| 2011/0233147 A1 | | 9/2011 | Hayafuji et al. |

OTHER PUBLICATIONS

Lindner, Nora, International Preliminary Report on Patentability dated May 14, 2008.
Young, Lee W., International Search Report dated Dec. 6, 2007.
Singh, N., et al., "Efficacy of chlorine dioxide, ozone, and thyme essential oil or a sequential washing in killing *Escherichia coli* O157:H7 on lettuce and baby carrots," Lebensm.-Wiss u.-Technol., 35, (2002) 720-729.
European Search Report EP 06 84 9144, Issued Aug. 6, 2013.
U.S. Office Action for U.S. Appl. No. 12/296,049, Dated Sep. 9, 2013.
U.S. Office Action for U.S. Appl. No. 13/365,885, Dated Aug. 29, 2013.
EPA Guidance Manual on Alternative Disinfectants and Oxidant: Chlorine Dioxide, Apr. 1999, p. 4-1:4-41.
Canadian Search Report CA 2,629,888, Issued Oct. 7, 2013.
U.S. Office Action for U.S. Appl. No. 13/365,869, Dated May 16, 2014.
U.S. Office Action for U.S. Appl. No. 13/365,885, Dated Jun. 10, 2014.
U.S. Office Action for U.S. Appl. No. 13/365,912, Dated May 16, 2014.
Canadian Office Action for CA 2,629,888, Dated Sep. 11, 2014.
U.S. Office Action for U.S. Appl. No. 12/296,049, Dated Sep. 26, 2014.
Canadian Office Action for CA 2,675,574 Dated Oct. 6, 2014.
Australian Office Action for Australian Patent Application No. 2006332600 mailed Dec. 20, 2010.
Australian Office Action for Australian Patent Application No. 2006332600 mailed May 6, 2011.
Bohner et al., Corrosivity of chlorine dioxide used as sanitizer in ultrafiltration systems, Journal of Dairy Science, 74 (10), 3348-3352, Oct. 1991.
Canadian Office Action for CA 2,629,888, dated Oct. 17, 2012.
Canadian Office Action for CA 2,675,574 dated Feb. 7, 2013.
Desai, U.J., "Comparative Analytical Methods for the Measurement of Chlorine Dioxide," Masters Thesis—Environmental Engineering, Virginia Polytechnic Institute and State University, Blacksburg, VA, 2002.
Entire patent prosecution history of U.S. Appl. No. 12/296,049, filed Apr. 21, 2010, entitled, "Storage-Stable Aqueous Solutions of Chlorine Dioxide and Methods for Preparing and Using Them."
Entire patent prosecution history of U.S. Appl. No. 12/296,051, filed Nov. 11, 2008, entitled, "Use of Storage-Stable Aqueous Solutions of Chlorine Dioxide to Generate Pure Chlorine Dioxide Gas for Decontamination."
Entire patent prosecution history of U.S. Appl. No. 13/365,869, filed Feb. 3, 2012, entitled, "Storage-Stable Aqueous Solutions of Chlorine Dioxide and Methods for Preparing and Using Them."
Entire patent prosecution history of U.S. Appl. No. 13/365,885, filed Feb. 3, 2012, entitled, "Storage-Stable Aqueous Solutions of Chlorine Dioxide and Methods for Preparing and Using Them."
Entire patent prosecution history of U.S. Appl. No., 13/365,912, filed Feb. 3, 2012, entitled, "Storage-Stable Aqueous Solutions of Chlorine Dioxide and Methods for Preparing and Using Them."
Finch, G.R., et al., "Synergistic Effects of Multiple Disinfectants," AWWA Research Foundation and American Water Works Association, 2000.
Harris, C.L., "The Effect of Predisinfection with Chlorine Dioxide on the Formation of Haloacetic Acids and Thihalomethanes in a Drinking Water Supply," Masters Thesis—Environmental Engineering, Virginia Polytechnic Institute and State University, Blacksburg, VA, 2001.
International Search Report dated Jul. 3, 2008 for International Application No. PCT/US2007/066081.
Li, H. et al., "Sequential Disinfection Design Criteria for Inactivation of Cryptosporidium Oocysts in Drinking Water," AWWA Research Foundation and American Water Works Association, 2001.
Noss, C.L. and V.P. Olivieri, "Disinfecting capabilities of oxychlorine compounds," Appl. Environ. Microbiol. 1985, vol. 50, No. 50, pp. 1162-1164.
Office Action, dated Dec. 16, 2013, corresponding to counterpart Canadian Patent Application No. 2675574.
Rosenblatt et al., "The Reaction of Chlorine Dioxide with Triethylamine in Aqueous Solution," J. Org. Chem. (1963) 28 10:2790-2794.
Water Boy 2011, Retrieved online at http://www.waterboyinc.com/blog/distilled-and-purified-water/.
White, G.C., "Handbook of Chlorination and Alternative Disinfectants," Wiley Interscience, 1999.
Written Opinion of the International Searching Authority mailed Jul. 3, 2008 for International Application No. PCT/US2007/066081.
Young, "Humidity Control in the Laboratory Using Salt Solutions-A Review," J. Appl. Chem. (1967) 17:241-245.

* cited by examiner

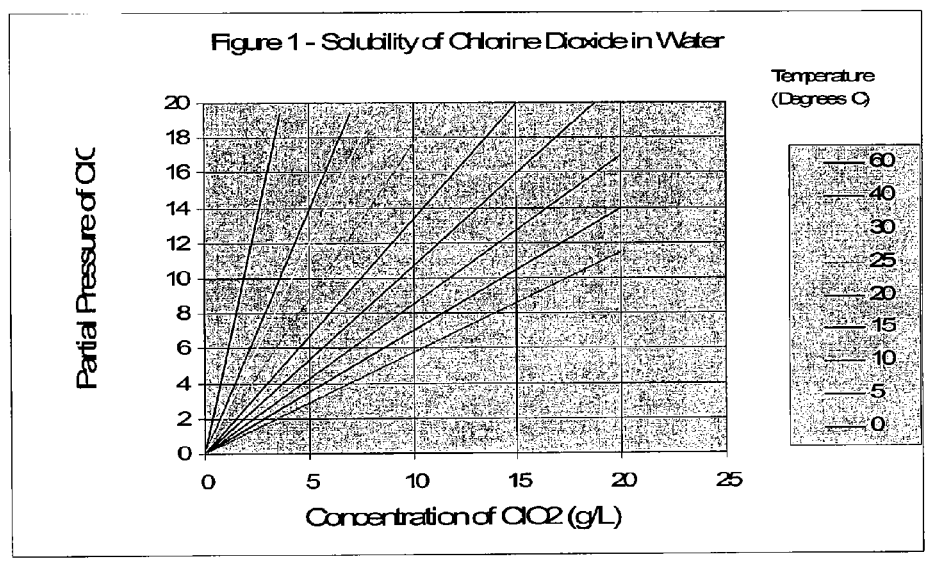

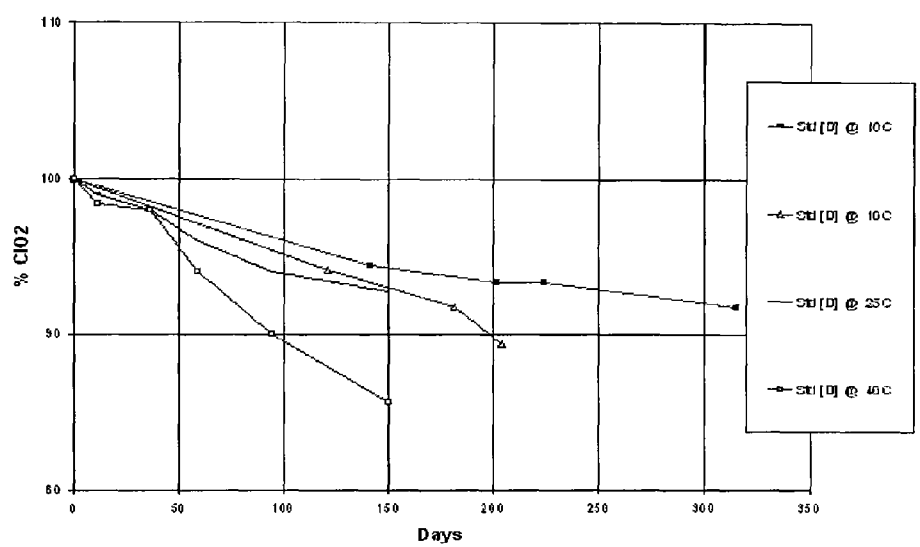
Figure 2: ClO$_2$ Stability In Glass Bottles Beginning At 4500 ppm

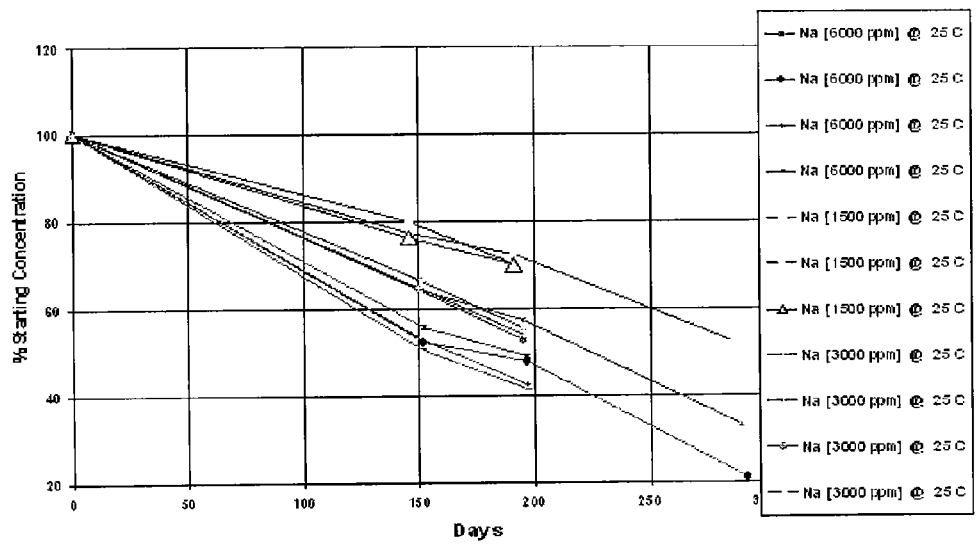
Figure 3: ClO$_2$ Stability In Glass Bottles Beginning At 3000 ppm

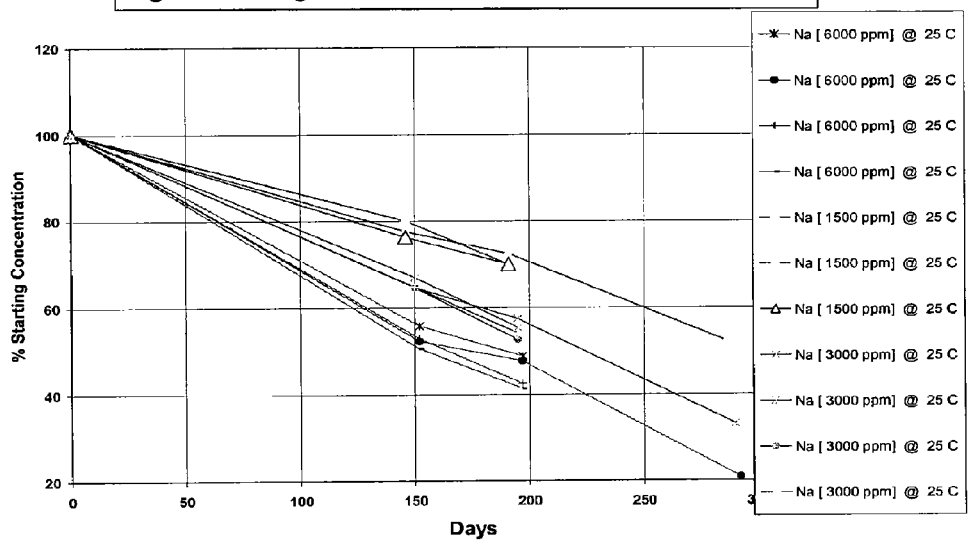

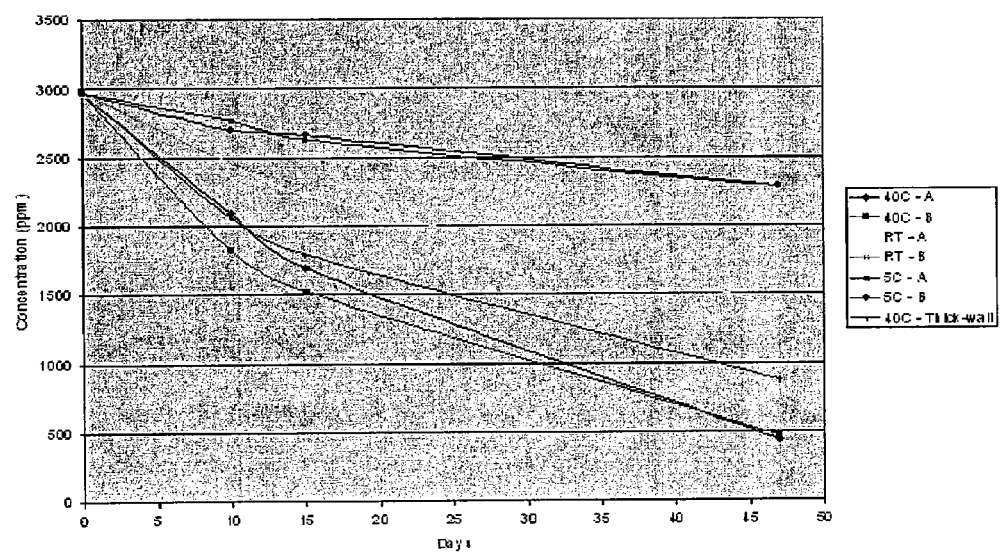
Figure 5: Solutions Stored In HDPE Bottles

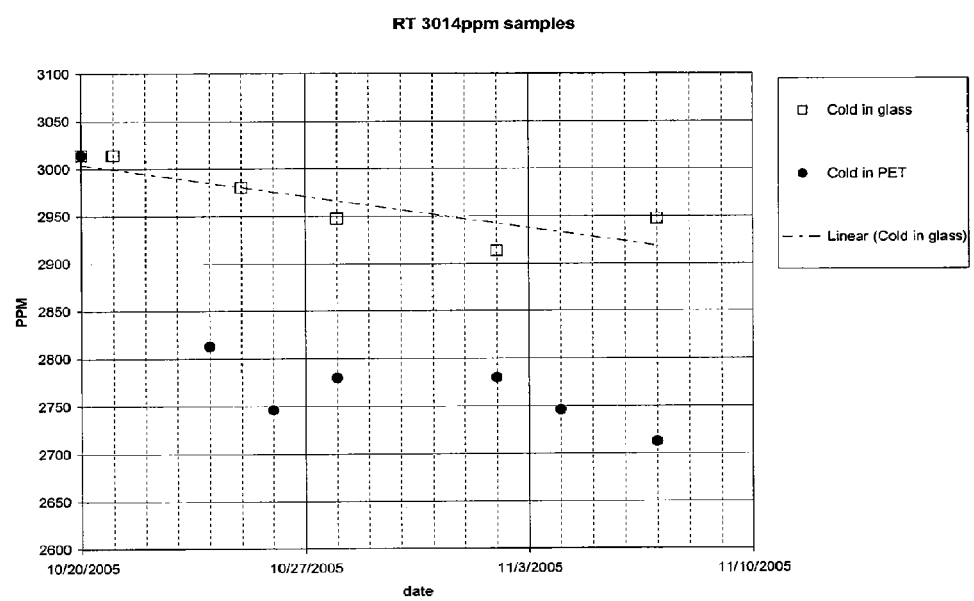
Figure 6 – Solutions Stored In PET Bottles

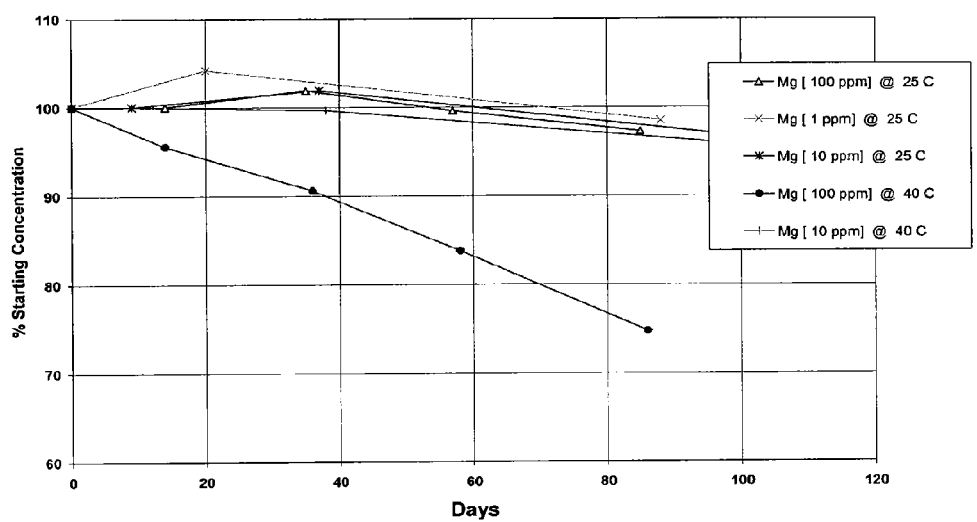
Figure 7 - Low Levels of MgCl2 in Deionized Water

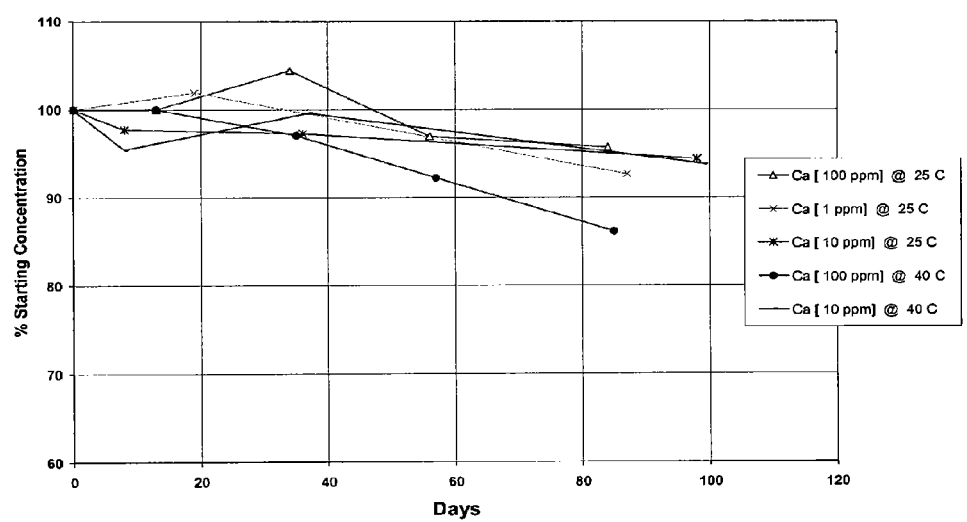

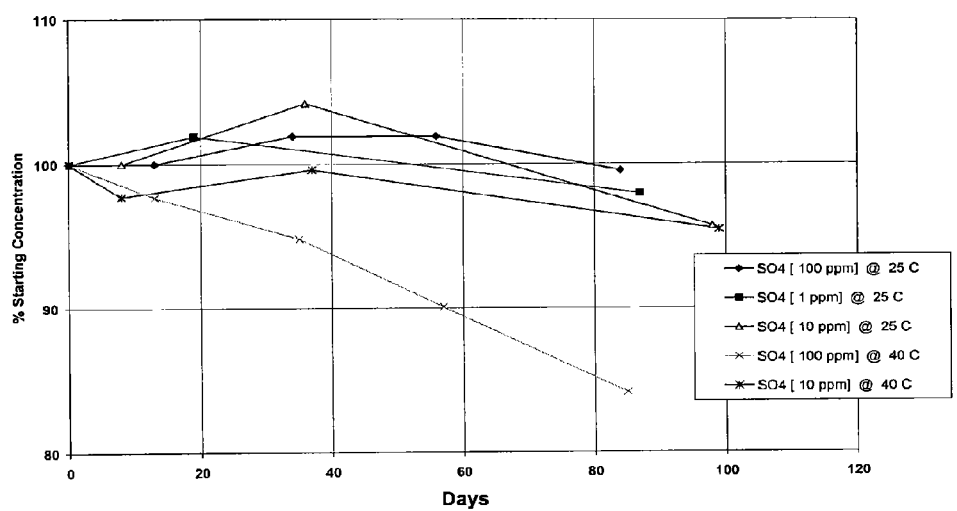

STORAGE-STABLE AQUEOUS SOLUTIONS OF CHLORINE DIOXIDE AND METHODS FOR PREPARING AND USING THEM

This application is a division of U.S. application Ser. No. 12/296,049, filed Apr. 21, 2010, which is a U.S. national phase filing of PCT Application No. US06/060879, filed Nov. 14, 2006, and claims priority of U.S. Provisional Application No. 60/736,636, filed Nov. 14, 2005, the entireties of which applications are incorporated herein by reference.

BACKGROUND

Chlorine dioxide is a strong, but highly selective oxidizer. It has been used in aqueous solution for many decades in various applications including disinfecting drinking water and in other water processing applications. One of its chief benefits is that it does not react with organic materials to form chlorinated hydrocarbons, which are increasingly avoided because of health concerns and regulatory pressure. In fact, chlorine dioxide can be used to destroy organic compounds that form chlorinated hydrocarbons, or to destroy chlorinated hydrocarbons after they have been formed.

Aqueous solutions of chlorine dioxide are also used in large quantities for bleaching paper pulp, where use of the chemical has greatly reduced the formation of chlorinated by-products compared to those formed by prior methods. Solutions of chlorine dioxide have been used extensively for decontamination of bio-contaminated buildings, enclosures, and articles. Chlorine dioxide solutions are also used extensively as a disinfecting wash for poultry, beef, and many types of fruits and vegetables. Because of the instability of known chlorine dioxide solutions, these solutions are produced at or near the point of use, and storage times are limited.

Several suppliers offer a liquid called "Stabilized Chlorine Dioxide", "Chlorine Dioxide Solution" or similar names. These materials are not chlorine dioxide, but dissolved sodium chlorite. When mixed with acid, they produce chlorine dioxide solutions, but this requires chemical mixing and handling of acid. Opportunities abound for errors in mixing and even when reagents are mixed properly the resulting solution may contain high levels of salt, acid, and other impurities. Moreover, after mixing, the chlorine dioxide solutions have a short shelf life.

Gaseous chlorine dioxide is also becoming an increasingly important disinfectant. The gas has been used for many years to sterilize medical instruments and other medical articles as described in U.S. Pat. No. 4,681,739. Gaseous chlorine dioxide has also been used to decontaminate buildings containing Anthrax spores after the Anthrax attacks of 2001. The gas reportedly has been commonly used for decontamination of buildings infested with mold. It is also being introduced as a decontaminant for bio-safety cabinets and other laboratory enclosures.

Chlorine dioxide can be produced in a variety of ways. Most of the production processes suitable for use at less than a few thousand pounds per day are based on reaction of sodium chlorite with chlorine or acid in aqueous solution. Many of these processes are based on the reaction:

$2NaClO_2 + Cl_2 \Rightarrow 2ClO_2 + 2NaCl$  Reaction 1

All technologies where chlorine dioxide is produced in solution, whether produced from Reaction 1 or otherwise, produce chlorine dioxide solutions containing the other products and by-products of the reaction plus unreacted feedstock reagents. Typical contaminants in these products include chlorine, various acids, sodium chlorite, sodium chlorate, and sodium chloride.

In recent years, a new process described in U.S. Pat. No. 5,234,678, has enabled the simple and safe production of high purity chlorine dioxide gas. This process involves the reaction of a solid granular sodium chlorite with dilute chlorine gas according to Reaction 1. Unlike the liquid phase production methods, the product resulting from this process does not contain significant quantities of sodium chlorite, sodium chlorate, or substantial quantities of sodium chloride, since these materials do not form gases to any appreciable extent. Tests by an independent lab have shown that the chlorine dioxide gas produced from this process can be over 99.95% pure.

The use of highly pure chlorine dioxide gas as an oxidizer and disinfectant has been limited because chlorine dioxide is unstable in gas phase, and has been thought to have limited stability in aqueous solution. The Handbook of Chlorination and Alternative Disinfectants—$4^{th}$ Edition—George Clifford White, states that "aqueous solutions of chlorine dioxide are subject to photolytic decomposition, the extent of which is a function both of time and of the intensity of the ultraviolet component of the light source. Aqueous solutions of chlorine dioxide are known to retain their strength for longer periods of time if kept cool and properly stored in the dark." For many applications, however, refrigeration is expensive or impractical, and even with refrigeration the shelf life of chlorine dioxide produced in traditional ways is relatively short. For these reasons, most chlorine dioxide applications currently require generation of the chemical at, or near, the point of use. The literature abounds with references stating that unrefrigerated chlorine dioxide cannot be shipped or stored.

The use of chlorine dioxide solutions has been limited because chlorine dioxide concentration must be kept low for safety reasons. Chlorine dioxide gas above such solutions can decompose spontaneously and exothermically if it reaches elevated concentrations. OSHA lists the safe limit as 10% (76 mm partial pressure) in air at atmospheric pressure. Other expert sources identify the limit as 16% (120 mm partial pressure) or even higher. At a partial pressure of 150 mm and higher, a spontaneous decomposition is quite mild and characterized as a "puff". At still higher concentrations, the decompositions become explosive, and at partial pressures of 225-300 mm or higher, explosions can be quite violent. The presence of water vapor elevates the concentration at which decompositions occur. FIG. 1 shows the vapor pressure of chlorine dioxide gas above aqueous solutions of the gas as a function of temperature and concentration. As with aqueous solutions of most gases, the solubility of chlorine dioxide decreases as temperature increases—i.e. for a given concentration of dissolved gas, the partial pressure of the gas above the solution at equilibrium is a positive function of temperature.

Even if the concentration of a solution is in a stable range, the shipment and storage of chlorine dioxide solutions must be done with care. It is commonly thought that chlorine dioxide cannot be shipped or stored. Thus, methods are needed for safely shipping and storing chlorine dioxide solutions.

For economic and logistical reasons, it is desirable to ship the most concentrated solutions that can safely be shipped. However, solutions packaged at low temperature under safe conditions might warm up and produce dangerous gas-phase concentrations. For example, solutions packaged at 5° C. and 15 g/L would have a headspace gas concentration of about 11 kPa (84 mm Hg partial pressure), which would be safe. If that same solution warmed up to 20° C., the headspace concentration would reach 20 kPa, which is near the region of spontaneous decomposition. If that solution warmed further to 60° C., the gas phase concentration could become quite dangerous. Solutions having a concentration below 3000 ppm by weight chlorine dioxide in water are regarded as safe for shipment in temperate climates. The gas in the head space above these liquids might reach 110-115 mm Hg if the temperature of the liquid reached 60° C. Solutions up to 2500 ppm could safely be allowed to reach 71° C., which is as high as temperatures are likely to reach in North America or Europe, even in unventilated enclosures in the sun. The use of ventilated warehouses and trucks, could permit still higher concentrations to be used. If the containers of solution could be reliably cooled, even without refrigeration, much higher concentrations are feasible. The extent to which water vapor elevates the safe concentration remains to be tested, but the fact that the gas in the head space of such containers will be saturated with water vapor provides an extra margin of safety.

SUMMARY

Extremely pure solutions of chlorine dioxide, methods for making such solutions and compositions and methods for storing and shipping such solutions and methods of using such solutions are disclosed. Generally, the chlorine dioxide solutions of the invention are aqueous solutions containing about 2500 ppm or less of total impurities, more preferably 1000 ppm or less, more preferably about 500 ppm or less, even more preferably about 250 ppm or less and yet more preferably, about 100 ppm or less of total impurities. Such solutions can be prepared by dissolving a pure chlorine dioxide gas in pure water. The chlorine dioxide gas solution can be prepared by passing dilute highly pure chlorine gas through a bed of substantially solid sodium chlorite and contacting the resulting chlorine dioxide gas with pure water. Systems for generating ultra-pure chlorine dioxide gas are available from CDG Research Corporation of Bethlehem, Pa. Suitable water can be prepared from municipal drinking water or other water which can be purified by distillation, reverse osmosis, or ion exchange. Chlorine dioxide solutions can then be stored in containers that minimize loss of chlorine dioxide. Preferably the containers are flexible containers and have a head space over the stored chlorine dioxide solution of about 1 percent of the volume of the container or less.

For purposes of this specification ppm is parts per million by weight. It can be appreciated however, that the concentration of dissolved chlorine dioxide will depend on the temperatures the solution is likely to experience as well as the humidity. In an embodiment the concentration of dissolved chlorine dioxide is in the range of about 100 to about 800 ppm, more preferably to about 5,000 ppm, or even more preferably about 4,000 ppm or even about 3,000 ppm by weight.

In an embodiment the solution can be prepared by contacting chlorine dioxide gas with water having the chlorine dioxide gas can have a concentration in the range of about 1 to about 15% by volume in a gas, such as an inert gas, nitrogen or air, with water. Preferably, the water contains about 1000 ppm or more preferably about 500 ppm or less of contaminants by weight. The chlorine dioxide gas can be contacted with water by any suitable method that does not introduce contaminants or result in excessive loss. For example, the gas can be bubbled through the water, such as with a sparger. Alternatively, the solution can be prepared in a packed column with a flowing gas and flowing water such that the flowing gas flows up through the column as water trickles down over the packing in the column and the dissolved chlorine dioxide solution can be collected as the effluent from the bottom of the column. Such columns and packing can be obtained from Koch Glitsch, Inc. of Wichita Kans., for example.

In an embodiment the chlorine dioxide solutions can be stored at temperatures below room temperature or about 20° C., preferably below about 15° C., more preferably below about 10° C. and even more preferably below about 5° C.

The solutions can be used in any number of applications. For example the solutions can be diluted and used in topical treatments by contacting human skin, nails, wounds, and lesions with an amount of the solution. Diseases can be selected from the group of diseases caused by bacteria, viruses, and fungi. The solutions can be used in various water treatment applications by contacting water with an amount of the solution to reduce the amount of viable bacteria, viruses or fungi. Such water can include potable water, waste water, or recirculating water as is found in cooling towers or other recirculating water systems. The solutions can also be used to treat hard surfaces such as food preparation surfaces or surfaces in houses or buildings to reduce bacterial, viral or fungal loads.

Containers are also disclosed for holding chlorine dioxide solutions made of materials and with wall thickness such that the rate of chlorine dioxide loss from the container is reduced. In an embodiment, the container can be a glass bottle, ideally a bottle in which the glass is formulated to minimize transmission of ultraviolet light. In an embodiment the container can be made of a biaxially oriented polymer such as polyethylene terepthalate. In another embodiment, the container can be made from high density polyethylene (HDPE) such as is used in making plastic 55-gallon drums.

In an embodiment such a container can contain a solution of chlorine dioxide having a concentration the range of about 100 to about 8000 ppm, or more preferably about 5,000, or even more preferably about 4,000, or even about 3,000 by weight and the container can be flexible and have a gaseous headspace of about 1% of the container volume or less.

Provided that such chlorine dioxide solutions are stored in flexible containers with no head space, they can be safely shipped and stored at concentrations that would otherwise be unsafe because the partial pressure of gas above the solution will always be less than 1 atmosphere over a very wide range of concentrations and temperatures, and since the pressure on the outside of the container will always be 1 atmosphere (adjusted for altitude), bubbles of concentrated chlorine dioxide cannot form inside the container. If the flexible container is not completely filled, then the container can withstand thermal expansion of the liquid and even mild exothermic decompositions in stray bubbles, if such were to occur.

Additional features and advantages are described herein, and will be apparent from, the following Detailed Description and the Figures.

BRIEF DESCRIPTION OF THE FIGURES

FIG. 1 provides a graphical representation of the dependence of $ClO_2$ partial pressure versus concentration in water as a function of temperature.

FIG. 2 provides a graphical representation of aqueous chlorine dioxide concentration when stored in amber glass bottles as a function of time and temperature with an initial chlorine dioxide concentration of about 4500 ppmw (parts per million by weight).

FIG. 3 provides a graphical representation of aqueous chlorine dioxide concentration beginning at 3000 ppmw with salt at concentrations of 1500 ppmw 3000 ppmw, and 6000 ppmw in amber glass bottles as a function of time and temperature. 3000 ppmw chlorine dioxide and 2600 ppmw NaCl are approximately equimolar concentrations, such as would be produced in Reaction 1, if the reaction were carried out at perfect stoichiometric conditions.

FIG. 4 provides a graphical illustration of the stability of chlorine dioxide in an equimolar chlorine dioxide NaCl concentration at 3900 ppm chlorine dioxide.

FIG. 5 provides a graphical illustration of the stability of chlorine dioxide in aqueous solutions with 19% NaCl by weight at different temperatures.

FIG. 6 provides a graphical illustration of the stability of chlorine dioxide in aqueous solutions with 19% NaCl by weight and 4500 ppmw chlorine dioxide.

FIG. 7 provides a graphical illustration of the stability of chlorine dioxide in aqueous solutions containing various concentrations of $MgCl_2$.

FIG. 8 provides a graphical illustration of the stability of chlorine dioxide in aqueous solutions containing various concentrations of $CaCl_2$.

FIG. 9 provides a graphical illustration of the stability of chlorine dioxide in aqueous solutions containing various concentrations of $Na_2SO_4$.

DETAILED DESCRIPTION

New storage-stable solutions of chlorine dioxide and methods for producing, storing, transporting and using them are disclosed. In an embodiment, the solutions consist of suitably pure water with an ultra-high-purity chlorine dioxide gas dissolved therein. These solutions can be prepared by contacting the pure water with ultra-pure chlorine dioxide. Any method for contacting the water with chlorine dioxide gas can be used so long as the gas dissolves in the water and the process does not introduce undesirable impurities into the solution. For example, this may be accomplished by bubbling the gas through the water. Alternatively, a counter-current packed column contactor can be employed such that water trickles down from the top of the column over packing while gas flows upward from the bottom of the column and chlorine dioxide solution drains from the bottom of the column.

Any suitable pure water can be used. Suitable water lacks substantial quantities of impurity that causes the shelf life of the aqueous chlorine dioxide to deteriorate below a desired shelf life. Suitable water can include deionized, distilled or water prepared by reverse osmosis or by a combination of these methods.

Chlorine dioxide solutions can deteriorate in by chemical degradation into chlorine, oxygen, chlorite, chlorate, or other decomposition products. Traditionally, it has been believed that this mechanism prevented long shelf life for chlorine dioxide solutions. The present invention is based in part on the surprising discovery that these decomposition reactions either do not occur or occur at very slow rates in solutions made of pure water and ultra-pure chlorine dioxide. Solutions made by reacting liquid reagents according to reaction 1 yield chlorine dioxide in addition to sodium chloride in an equimolar concentration, and possibly unreacted sodium chlorite and/or unreacted chlorine gas.

FIG. 2 shows the stability of solutions of pure chlorine dioxide at about 3000 ppmw in pure water at various temperatures. Even at 40° C., the solution retains about 90% or more of its starting concentration for more than 90 days. This is considered commercially acceptable.

FIG. 3 shows the concentration of pure chlorine dioxide in amber glass bottles as a function of time and temperature at different low levels of contamination with sodium chloride (NaCl). These studies show that, these chlorine dioxide solutions retain about 90% or more of their starting concentration for at least about 90 days except for the sample with 100 ppmw concentration of NaCl.

FIG. 4 shows the effect of salt at concentrations in a range that would comprise concentrations that would be produced if the solution had been prepared in a solution-based generator, for example a generator where reaction 1 is carried out in solution. These studies demonstrate that salt substantially increases the rate of chlorine dioxide decomposition in solution and the resulting solutions do not retain the target concentration of 90% starting concentration for at least 90 days.

Permeation of chlorine dioxide through the walls of a container occurs with many forms of container materials. Common plastics such as polyethylene, polypropylene and polycarbonate are known to be permeable to chlorine dioxide. If solutions are packaged in containers of these materials, the concentration of the chlorine dioxide will slowly decrease as it diffuses into and through the walls of the container. This process can be substantially eliminated by selection of the appropriate materials with an appropriate thickness. Testing of chlorine dioxide loss rates can be used to identify suitable materials for storage containers. FIG. 5 shows the chlorine dioxide concentration decrease as a function of time at various temperatures in 500 mL HDPE (high density polyethylene) bottles. In FIG. 5 "A" and "B" represent the results from separate but identical studies. This study demonstrated that the rate of loss of chlorine dioxide is a strong function of temperature. One of the curves in FIG. 5 is for a thick-walled HDPE bottle where the wall thickness is similar to that used in 55 gallon HDPE drums. This study further demonstrates that the loss rate of chlorine dioxide diffusion through the thick wall container is slower than through the thin walled container. This study also demonstrates that the rate of loss in the thick-wall bottle is initially equal to that in the thin. It is possible that this is because the rate of loss is initially determined by the rate at which gas diffuses into the inner surface of the bottle which is relatively fast. That rate would be the same for thick bottles as for thin. As time goes by, the wall becomes "saturated" and diffusion into the inner wall equals diffusion out of the outer wall. In this case, diffusion is slower through the thick wall. Because loss of concentration by permeation through the container walls is an inverse function of surface to volume ratio of the container, the rate of concentration loss through the walls of an HDPE 55 gallon drum or larger HDPE container is negligible compared to the concentration decay due to other factors.

The effect of sodium chloride on the stability of chlorine dioxide solutions is very surprising. Although the shelf life of chlorine dioxide solutions can be affected by chemical "demand" in the water, sodium chloride would not theoretically exert any demand. It has been hypothesized that the presence of high levels of sodium chloride causes the reversal of Reaction 1 to re-form sodium chlorite and chlorine. Analysis of samples that have degraded because of the presence of sodium chloride shows the presence of significant quantities of chlorite ion, while none, is detectable in the pure (unsalted) samples. However, the stoichiometry does not fully explain the amount of degradation apparent in FIG. 2. This demonstrates that additional factors are present that can lead to chlorine dioxide loss.

In many commercial applications, a shelf life of just a few days is adequate. For these applications small HDPE containers can be used for storage of aqueous chlorine dioxide. Desirably containers such as large 5 gallon or 55 gallon drums or even larger HDPE containers can be used to store chlorine dioxide solutions. Such containers, prior to use, can be pretreated by filling with a pre-treatment solution containing chlorine dioxide or with dilute chlorine dioxide gas prior to filling with solution. This saturates the walls with chlorine dioxide and greatly slows initial chlorine dioxide losses. Shelf-life can be further extended by storing and shipping the filled containers under refrigeration.

Other types of plastic containers exhibit superior barriers to permeation by chlorine dioxide from aqueous solutions. FIG. 8 shows the decay in concentration of solutions made with distilled water and stored in 750 mL bottles made of PET (polyethylene terephthalate), a biaxially oriented polymer. After an initial rapid rate of loss, the solution in PET bottles is almost as stable as that stored in glass. Thus, after adjusting for the initial concentration loss, this study demonstrates that a solution of chlorine dioxide is storage stable in PET bottles.

EXAMPLE

For the purposes of the experiments described in the examples the phrase "pure chlorine dioxide" means chlorine dioxide produced as gas in a process described in U.S. Pat. No. 5,234,678, which are more than 99% pure. This chlorine dioxide gas can be diluted in air or nitrogen and the process has been shown by testing in an independent laboratory to produce dilute chlorine dioxide that is greater than 99.97% chlorine-free with no detectable chlorine at the limits of detection. Since the other reagents and potential products of the process substantially do not exist as gases, this is substantially pure chlorine dioxide gas.

"Pure water" means water purified through distillation, deionization, or reverse osmosis so that it contains less than about 1 ppm of solid impurities.

Solutions of chlorine dioxide were prepared by dissolving chlorine dioxide gas in pure water. Unless otherwise noted, the starting concentration of the solutions tested was about 3000 ppm chlorine dioxide ±5%. Data in herein are reported as % of starting concentration unless otherwise noted.

All data on concentration of aqueous solutions were measured by amperometric titration as described in EPA Standard Methods. Serial dilution was used to adjust to the range of the analytical device.

The accuracy of the analytical technique used is ±3%. Any variation of less than 3% is not considered significant. Apparent increases in concentration in a sealed container are attributable to measurement variability.

Loss of less than about 10% of starting concentration after about 90 days at elevated temperature is considered to represent commercially acceptable shelf life. This is much better than the reported shelf life of other common disinfectants such as sodium hypochlorite at comparable temperatures.

FIG. 2 shows the concentration of chlorine dioxide in distilled water in amber glass bottles as a function of time and temperature. FIG. 2 demonstrates surprising stability of aqueous chlorine dioxide solutions over the duration of the test. Further, the figure shows the temperature dependence of the chlorine dioxide loss within the range of 10° C. to about 40° C. In each case the solutions had a commercially acceptable shelf life. This data also shows that refrigerated solutions may have a shelf life of about a year or more. FIG. 2 includes data for chlorine dioxide solutions in pure water with no added compounds.

FIG. 3 shows the effect of low levels of sodium chloride contamination on solutions of pure chlorine dioxide dissolved in otherwise pure water. Concentrations reported in the legend are concentrations of sodium ion. These samples were aged at 25 and 40° C. At 25° C. and up to 100 ppm NaCl, the samples were equally stable within the margin of error. At 100 ppm $Na^+$ and 40° C. the chlorine dioxide deteriorated at a markedly higher rate. Similar tests done using $CaCl_2$ (reported as concentration of $Ca^{++}$), $MgCl_2$ (reported as concentration of $Ca^{++}$), and $Na_2SO_4$ (reported as concentration of $SO^{-2}$) show similar patterns (FIGS. 7, 8 & 9) The test using $Na_2SO_4$ suggests that the accelerated deterioration of the chlorine dioxide at 40° C. and 100 ppm is due to the concentration of alkali metal ions or total ionic concentration rather than chloride ion alone.

This data indicates that 3000 ppm solutions of pure chlorine dioxide in water having less than 10 ppm contamination with alkali metal salts lose less than about 10% of their concentration in about 100 days at temperatures up to 40° C., while the same solutions having alkali metal salts at 100 ppm deteriorate at a much higher rate at 40° C. There is no statistically significant difference in the stability of the solutions at different temperatures and salt concentrations for temperatures of less than about 25° C. or concentrations of less than about 10 ppm. Only the combination of high temperature and high concentration accelerated decomposition. For much higher concentrations such as 1500-6000 ppmw of salt, the loss of concentration was much higher than for salt concentrations of about 100 ppmw or less, even at room temperature.

Chlorine dioxide solutions made by reacting sodium chlorite with chlorine in aqueous solution, which produces high concentrations of sodium chloride, are much less stable than solutions made using pure chlorine dioxide and pure water.

The invention is claimed as follows:

1. An apparatus for holding aqueous chlorine dioxide comprising: a storage container and a stable aqueous solution of chlorine dioxide containing about 1000 ppm or less of total impurities, wherein a starting concentration of chlorine dioxide in the solution is about 2000 ppm to 4500 ppm by weight, and wherein the solution retains at least 90% of the starting concentration of chlorine dioxide after 90 days at 40° C. when sealed within the storage container.

2. The apparatus of claim 1, wherein the container comprises high density polyethylene.

3. The apparatus of claim 1, wherein the container further comprises an inner surface treated with a chemical to reduce the rate of chlorine dioxide loss prior to addition of the chlorine dioxide solution, wherein the chemical used to treat the container is selected from the group of chemicals consisting of chlorine dioxide, chlorine and fluorine.

4. The apparatus of claim 1, wherein the container comprises glass.

5. The apparatus of claim 1, wherein the container comprises biaxially oriented polymers.

6. The apparatus of claim 1, wherein the container comprises polyethylene.

7. The apparatus of claim 1, wherein the container comprises polyethylene terephthalate.

8. The apparatus of claim 1, wherein the container has a temperature of about 20° C. or less.

9. The apparatus of claim 1, wherein the concentration of chlorine dioxide in the container is about 2500 ppm to 4500 ppm by weight and the container is flexible and has a gaseous headspace of about 1% of the container volume or less.

10. An apparatus for holding aqueous chlorine dioxide comprising:
a storage container; and
a stable aqueous solution of chlorine dioxide containing a starting concentration of about 2500 ppm by weight or more of chlorine dioxide in water and 1000 ppm or less of total impurities;

wherein said container is capable of storing said aqueous solution of chlorine dioxide for at least 90 days at a temperature up to 40° C. and retaining at least 90% of the starting concentration of chlorine dioxide when sealed within the storage container.

11. The apparatus of claim 10, wherein the container comprises high density polyethylene.

12. The apparatus of claim 10, wherein the container further comprises an inner surface treated with a chemical to reduce the rate of chlorine dioxide loss prior to addition of the chlorine dioxide solution, wherein the chemical used to treat the container is selected from the group of chemicals consisting of chlorine dioxide, chlorine and fluorine.

13. The apparatus of claim 10, wherein the container comprises glass.

14. The apparatus of claim 10, wherein the container comprises biaxially oriented polymers.

15. The apparatus of claim 10, wherein the container comprises polyethylene.

16. The apparatus of claim 10, wherein the container comprises polyethylene terephthalate.

17. The apparatus of claim 10, wherein the concentration of chlorine dioxide in the container is about 3000 ppm by weight and the container is flexible and has a gaseous headspace of about 1% of the container volume or less.

* * * * *